(12) United States Patent
Eom et al.

(10) Patent No.: US 11,682,184 B2
(45) Date of Patent: Jun. 20, 2023

(54) APPARATUS AND METHOD FOR ESTIMATING BIO-INFORMATION, AND OPTICAL SENSOR

(71) Applicant: SAMSUNG ELECTRONICS CO., LTD., Suwon-si (KR)

(72) Inventors: Kun Sun Eom, Yongin-si (KR); Yoon Jae Kim, Seoul (KR); Hyun Seok Moon, Hwaseong-si (KR); Jin Young Park, Hwaseong-si (KR); Myoung Hoon Jung, Bucheon-si (KR); Jeong Eun Hwang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 17/667,803

(22) Filed: Feb. 9, 2022

(65) Prior Publication Data
US 2023/0146917 A1    May 11, 2023

(30) Foreign Application Priority Data
Nov. 11, 2021    (KR) .................. 10-2021-0154754

(51) Int. Cl.
*G06V 10/147*    (2022.01)
*G06V 40/00*    (2022.01)
*G06V 10/141*    (2022.01)
*G06V 40/10*    (2022.01)

(52) U.S. Cl.
CPC .......... *G06V 10/147* (2022.01); *G06V 10/141* (2022.01); *G06V 40/15* (2022.01)

(58) Field of Classification Search
CPC ..... G06V 10/147; G06V 10/141; G06V 40/15
See application file for complete search history.

(56) References Cited

U.S. PATENT DOCUMENTS

| 9,506,802 | B2 | 11/2016 | Chu et al. |
| 9,664,556 | B2 | 5/2017 | Chu et al. |
| 9,696,199 | B2 | 7/2017 | Chu et al. |
| 9,752,925 | B2 | 9/2017 | Chu et al. |
| 9,820,659 | B1 * | 11/2017 | Rulkov ............... A61B 5/6804 |
| 10,088,356 | B2 | 10/2018 | Chu et al. |

(Continued)

FOREIGN PATENT DOCUMENTS

| CN | 105895641 B | 12/2018 |
| JP | 2018-140039 A | 9/2018 |

(Continued)

OTHER PUBLICATIONS

Communication dated Sep. 5, 2022 by the European Patent Office in counterpart European Patent Application No. 22163855.4.

*Primary Examiner* — Lixi C Simpson
(74) *Attorney, Agent, or Firm* — Sughrue Mion, PLLC (57) ABSTRACT

An apparatus for estimating bio-information may include an optical sensor comprising a light emitter disposed on a substrate, and a plurality of light receiving groups which are arranged on a plurality of concentric circles on the substrate, at different distances from the light emitter, respectively, and a processor configured to drive one of the plurality of light receiving groups that is selected based on a type of the bio-information to be estimated, and estimate the bio-information of an object based on optical signals detected by the driven light receiving group.

20 Claims, 8 Drawing Sheets

(56) References Cited

U.S. PATENT DOCUMENTS

| | | | |
|---|---|---|---|
| 10,132,677 B2 | 11/2018 | Chu et al. | |
| 10,215,698 B2 | 2/2019 | Han et al. | |
| 10,416,079 B2 | 9/2019 | Magnussen et al. | |
| 10,687,718 B2 | 6/2020 | Allec et al. | |
| 10,760,955 B2 | 9/2020 | Chu et al. | |
| 2009/0326346 A1* | 12/2009 | Kracker | A61B 5/6846 |
| | | | 600/323 |
| 2016/0113530 A1 | 4/2016 | Nagahiro et al. | |
| 2016/0206251 A1* | 7/2016 | Kwon | A61B 5/14552 |
| 2016/0334332 A1 | 11/2016 | Magnussen et al. | |
| 2017/0035308 A1* | 2/2017 | Gulati | G01N 21/4795 |
| 2019/0090766 A1 | 3/2019 | Block et al. | |
| 2019/0090806 A1* | 3/2019 | Clavelle | A61B 5/02427 |
| 2020/0260972 A1 | 8/2020 | Han et al. | |
| 2020/0292378 A1* | 9/2020 | Nakata | G01J 1/0266 |
| 2020/0352478 A1 | 11/2020 | Park | |
| 2021/0022613 A1 | 1/2021 | Connor | |
| 2021/0059586 A1* | 3/2021 | Marriott | A61B 5/11 |

FOREIGN PATENT DOCUMENTS

| | | |
|---|---|---|
| KR | 10-2020-0032172 A | 3/2020 |
| KR | 10-2020-0100487 A | 8/2020 |

\* cited by examiner

APPARATUS AND METHOD FOR ESTIMATING BIO-INFORMATION, AND OPTICAL SENSOR

CROSS-REFERENCE TO RELATED APPLICATION(S)

This application claims priority from Korean Patent Application No. 10-2021-0154754, filed on Nov. 11, 2021 in the Korean Intellectual Property Office, the disclosure of which is incorporated herein by reference in its entirety.

BACKGROUND

1. Field

Apparatuses and methods consistent with example embodiments relate to non-invasively estimating bio-information.

2. Description of the Related Art

Recently, with the aging population, soaring medical costs, and a lack of medical personnel for specialized medical services, research is being actively conducted on the convergence of technology and health. Particularly, monitoring of the health condition of the human body is not limited to medical institutions, but is expanding to mobile healthcare fields that may monitor a user's health condition anywhere and anytime in daily life at home or office. Typical examples of bio-signals, indicating the health condition of individuals, include body composition such as heart rate, electrocardiography (ECG), oxygen saturation, heart rate variability (HRV), electromyography (EMG), electroencephalogram (EEG), blood pressure, blood glucose, body fat percentage, etc., nutrition information, physical activity, amount of exercise, sleep information, gene information, etc., and in order to conveniently measure the bio-signals in daily life, technology is being developed for greatly improving user convenience by providing various bio-signal sensors which are mounted on the platform of wearable devices and the like.

SUMMARY

According to an aspect of the present disclosure, there is provided an apparatus for estimating bio-information, the apparatus including: an optical sensor comprising a light emitter disposed on a substrate, and a plurality of light receiving groups which are arranged on a plurality of concentric circles on the substrate, at different distances from the light emitter, respectively; and a processor configured to drive one of the plurality of light receiving groups that is selected based on a type of the bio-information to be estimated, and estimate the bio-information of an object based on optical signals detected by the driven light receiving group.

A plurality of detectors included in each of the plurality of light receiving groups may be spaced apart from each other by a predetermined angle on a corresponding one of the plurality of concentric circles.

A reference line may extend from a center of the plurality of concentric circles to a point on a largest concentric circle among the plurality of concentric circles, and the plurality of detectors of the plurality of light receiving groups may be located at different angles from the reference line.

Each of the plurality of light receiving groups may include a same number of detectors.

A plurality of detectors in each of the plurality of light receiving groups may be arranged symmetrical to each other with respect to the light emitter.

Among the plurality of concentric circles, a radius of a smallest concentric circle is greater than or equal to 2 mm, and a radius of a largest concentric circle is smaller than or equal to 6 mm.

Among the plurality of light receiving groups, the processor drives a light receiving group corresponding to separation distances, which are predetermined for each bio-information, between the light emitter and the plurality of light receiving groups.

Based further on at least one of a luminous intensity of a light source, a concentration range of the bio-information to be estimated, and a state of the object, the processor drives at least one light receiving group among the plurality of light receiving groups.

The sensor may further include wiring that connects a plurality of detectors in each of the plurality of light receiving groups, and the processor may receive the optical signals detected by the plurality of detectors which are connected by the wiring in the driven light receiving group.

The optical sensor may further include a switch configured to individually control connection to a plurality of detectors included in each of the plurality of light receiving groups, a transimpedance amplifier configured to filter and amplify analog signals photoelectric converted by the plurality of detectors, and a converter configured to convert the analog signals into digital signals.

The optical sensor may further include a partition wall disposed between the light emitter and the plurality of light receiving groups on the substrate.

The apparatus may further include a cover surface configured to be contacted by contact with the object, and the cover surface may have a size greater than or equal to a diameter of a largest concentric circle, among the plurality of concentric circles.

The apparatus may further include a cover surface coming into contact with the object, and the cover surface may have at least one of Fresnel lens, a retroreflector, and a cover glass coated with an anti-reflective coating.

The light emitter may emit light in a plurality of wavelength ranges, wherein the processor may control the light emitter to emit light of different wavelengths over time.

According to an aspect of another example embodiment, there is provided a method of estimating bio-information, the method including: driving a light emitter including at least one or more light sources disposed at a center of a substrate; based on a type of bio-information to be estimated, driving one of a plurality of light receiving groups which are respectively arranged on a plurality of concentric circles at different distances from the light emitter; and estimating the bio-information of a user based on optical signals detected by the driven light receiving group.

According to an aspect of another example embodiment, there is provided an optical sensor including: a light emitter including at least one or more light sources disposed at a center of a substrate; and a plurality of light receiving groups which are respectively arranged on a plurality of concentric circles at different distances from the light emitter on the substrate.

A plurality of detectors of the plurality of light receiving groups may be spaced apart by predetermined angles from the light emitter.

A reference line may extend from the center of the substrate to a point on a largest concentric circle among the plurality of concentric circles, and the plurality of detectors of the plurality of light receiving groups may be located at different angles from the reference line.

Each of the plurality of light receiving groups may include a same number of detectors.

A plurality of detectors in each of the plurality of light receiving groups may be arranged symmetrical to each other with respect to the light emitter.

BRIEF DESCRIPTION OF THE DRAWINGS

The above and/or other aspects will be more apparent by describing certain example embodiments, with reference to the accompanying drawings, in which.

DETAILED DESCRIPTION

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit for performing at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Further, the "same" length or angle in each embodiment not only means that the length or angle is 100% identical, but also that the length or angle is substantially identical, although there is a slight difference.

Hereinafter, embodiments of an apparatus and method for estimating bio-information will be described in detail with reference to the accompanying drawings.

Figure 1:
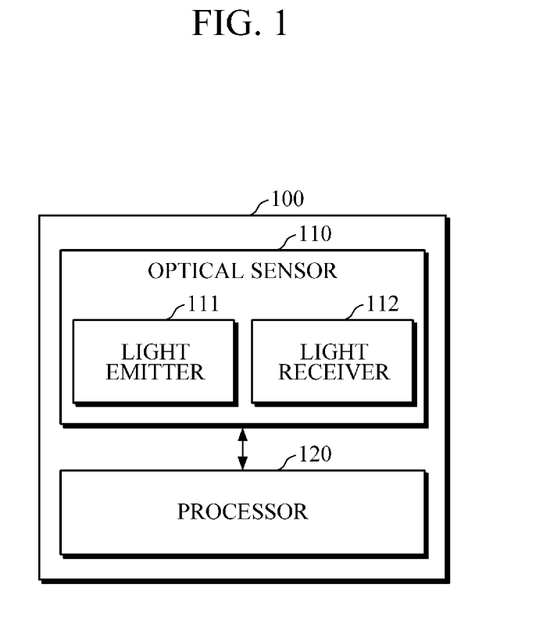
FIG. 1 is a block diagram illustrating an apparatus for estimating bio-information according to an example embodiment of the present disclosure.

FIG. 1 is a block diagram illustrating an apparatus for estimating bio-information according to an example embodiment of the present disclosure. The apparatus 100 for estimating bio-information may be mounted in a wearable device worn by a user, a cover of the wearable device, home appliances, such as a refrigerator, a smart mirror, etc., and various stand-alone products. In this case, examples of the wearable device may include a wristwatch-type wearable device, a bracelet-type wearable device, a wristband-type wearable device, a ring-type wearable device, a glasses-type wearable device, a headband-type wearable device, an earphone-type wearable device, etc., but the wearable device is not particularly limited in shape or size.

Referring to FIG. 1, the apparatus 100 for estimating bio-information includes an optical sensor 110 and a processor 120.

In particular, the bio-information may include blood pressure, including mean arterial pressure, systolic blood pressure, diastolic blood pressure, etc., heart rate, oxygen saturation, stress, blood glucose, antioxidant index, lactate, alcohol, cholesterol, triglyceride, etc., but is not limited thereto.

The optical sensor 110 may detect an optical signal from an object. In particular, the optical signal may include a photoplethysmography (PPG) signal for measuring a user's blood pressure and the like, or absorbance or absorption spectra for measuring oxygen saturation in blood or an antioxidant index of carotenoid accumulated in the epidermis, but is not limited thereto.

The object may be the skin surface of the wrist that is adjacent to the radial artery, and an upper part of the wrist where veins or capillaries are located, or peripheral parts of the body, such as fingers, toes, palm of the hand, sole of the foot, ears, forehead, and the like where blood vessels are densely located, but the object is not limited thereto.

The optical sensor 110 may include a light emitter 111 and a light receiver 112.

The light emitter 111 may include one or more light sources for emitting light onto the object. The plurality of light sources may emit light of the same wavelength or light of different wavelengths. In this case, the light sources may emit light of any one wavelength in a wavelength range from visible to infrared. For example, the light sources may emit light having any one wavelength in a wavelength range of 400 nm to 600 nm, but are not limited thereto. In this case, the light source may include at least one of a light emitting diode (LED), an LED array, a laser diode, a phosphor, etc., but is not limited thereto.

When the light emitted by the light emitter 111 is scattered or reflected from the object, the light receiver 112 may receive the light scatted or reflected from the object to detect an optical signal from the received light. In this case, the light receiver 112 may include a plurality of photodiodes, photo transistors (PTr), image sensors, e.g., a complementary metal-oxide semiconductor (CMOS) image sensor or a charge-coupled device (CCD) image sensor, and the like.

The light emitter 111 and the light receiver 112 may be disposed on a substrate of the optical sensor 110.

The light emitter 111 may be disposed at the center of the substrate, but is not limited thereto and may be disposed at a position spaced apart by a predetermined distance from the center of the substrate.

The light receiver 112 may include a plurality of light receiving groups positioned at different distances from the light emitter 111 on the substrate. The respective light receiving groups may include a plurality of detectors positioned at the same distance from the light emitter 111.

For example, the distances of the respective light receiving groups from the light emitter 111 may refer to distances from the center of the light emitter 111. For example, when the light emitter 111 may include a plurality of light sources (e.g., four LEDs) arranged on concentric circles, the distances from the light emitter 111 may refer to distances from the center of the concentric circles on which the four LEDs are arranged.

In another example, the optical sensor 110 may include a cover housing, and in order to allow the light emitted by the light emitter 111 to be transmitted through the object, the cover housing may include an optical open hole, through which light is transmitted, at a position corresponding to the light emitter 111. The optical open hole may be made of a transparent material, such as glass, plastic, and the like. In this case, the distances from the light emitter 111 may refer to distances from the center of the optical open hole.

As the light receiver 112 includes a plurality of light receiving groups positioned at different distances from the light emitter 111, it is possible to detect an optical signal from the object at an optimal separation distance between the light emitter 111 and the detector, which is predetermined for each type of bio-information to be estimated, thereby improving the accuracy in estimating bio-information. Further, the respective light receiving groups include a plurality of detectors disposed at different positions but the same distance from the light emitter 111, and by estimating bio-information using the detectors, measurement deviations caused by inhomogeneous distribution of skin pigment may be reduced.

The respective light receiving groups may include the same number of detectors, but are not limited thereto and may include different numbers of detectors. The detectors in the respective light receiving groups may be arranged symmetrical to each other with respect to the light emitter 111, but are not limited hereto.

The plurality of light receiving groups may be arranged to surround the light emitter 111.

In this case, the respective light receiving groups may be positioned at different distances from the light emitter 111. For example, the respective light receiving groups may be arranged on a plurality of concentric circles at different distances from the light emitter 111. In this case, the radius of a smallest concentric circle may be greater than or equal to 2 mm, and the radius of a largest concentric circle may be smaller than or equal to 6 mm, but the concentric circles are not limited thereto, and the size of each concentric circle may be changed variously. In addition, rather than being arranged on the plurality of concentric circles, the plurality of light receiving groups may be arranged, for example, on polygons, such as a plurality of triangles, squares, pentagons, etc., which are positioned at different distances from the light emitter 111.

For example, the corresponding detectors among the light receiving groups may be arranged in a straight line from the light emitter 111.

In another example, the respective detectors of the light receiver 112 may be arranged spirally with respect to the light emitter 111. A shape of the respective detectors of the light receiver 112, which are arranged spirally with respect to the light emitter 111, will be described in detail below with reference to FIG. 2.

Figure 2:
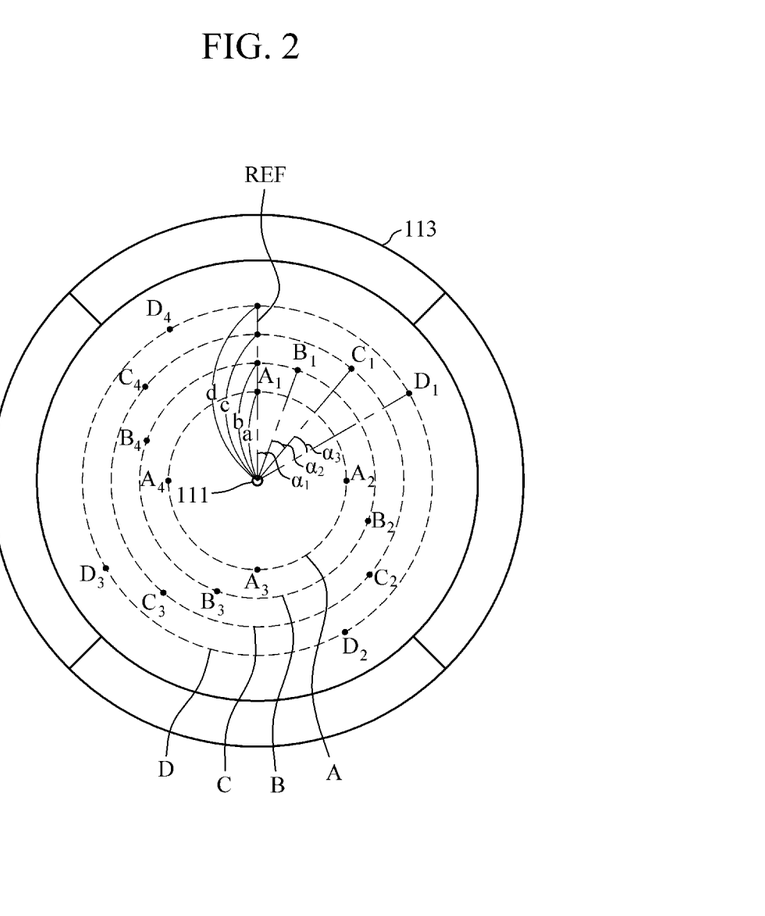
FIG. 2 is a plan view of an optical sensor according to an example embodiment of the present disclosure.

FIG. 2 is a plan view of an optical sensor according to an example embodiment of the present disclosure. Referring to FIG. 2, the light emitter 111, a first light receiving group (e.g., a first set of light detectors) of A1 to A4, a second light receiving group (e.g., a second set of light detectors) of B1 to B4, a third light receiving group (e.g., a third set of light detectors) of C1 to C4, a fourth light receiving group (e.g., a fourth set of light detectors) of D1 to D4, and a substrate 113 are illustrated.

While FIG. 2 illustrates the substrate 113 having a circular shape, the shape of the substrate 113 is not limited thereto, and may be, for example, a polygonal shape such as a triangle, a square, a pentagon, and the like.

While FIG. 2 illustrates an example in which the light emitter 111 is disposed at the center of the substrate 113, the light emitter 111 is not limited thereto and may be disposed at a position spaced apart by a predetermined distance from the center of the substrate 113.

While FIG. 2 illustrates an example in which the light receiver includes four light receiving groups, each including four detectors, and the detectors in the respective light receiving groups are arranged symmetrical to each other with respect to the light emitter 111, the number of the light receiving groups included in the light receiver, the number of the detectors included in the respective light receiving groups, and an arrangement shape of the detectors in the light receiving groups, and the like are not limited thereto.

Referring to FIG. 2, the first light receiving group of A1 to A4 is arranged on a first concentric circle A which is positioned at distance a from the light emitter 111; the second light receiving group of B1 to B4 is arranged on a second concentric circle B which is positioned at distance b from the light emitter 111; the third light receiving group of C1 to C4 is arranged on a third concentric circle C which is positioned at distance c from the light emitter 111; and the fourth light receiving group of D1 to D4 is arranged on a fourth concentric circle D which is positioned at distance d from the light emitter 111. The light detectors A1-A4 of the first light receiving group may be disposed to have the same separation angle (e.g., 90 degrees) between each other, on the first concentric circle A. Similarly, the light detectors B1-B4 of the second light receiving group may be disposed to have the same separation angle (e.g., 90 degrees) between each other, on the second concentric circle B, the light detectors C1-C4 of the third light receiving group may be disposed to have the same separation angle (e.g., 90 degrees) between each other, on the third concentric circle C, and the light detectors D1-D4 of the fourth light receiving group may be disposed to have the same separation angle (e.g., 90 degrees) between each other, on the fourth concentric circle D. While the separation angle between the light detectors that belong to the same light receiving group may be the same, the angle from the light emitter 111 to each of the light detectors A1-A4, B1-B4, C1-C4, and D1-D4 may be different from each other. While it is illustrated that the distances of the respective light receiving groups from the light emitter 111 are distances from the center of the light emitter 111, the distances of the respective light receiving groups from the light emitter 111 may also be distances from the center of an optical open hole of a cover housing of the optical sensor, as illustrated in FIG. 1.

In this case, as described above, radius a of a smallest concentric circle A is greater than or equal to 2 mm, and radius d of a largest concentric circle D is smaller than or equal to 6 mm, but the radiuses are not limited thereto.

In addition, a distance b-a between the first concentric circle A and the second concentric circle B, a distance c-b between the second concentric circle B and the third concentric circle C, and a distance d-c between the third concentric circle C and the fourth concentric circle D may be equal to or different from each other. For example, as the distance from the light emitter 111 increases, the distance between adjacent concentric circles may gradually increase or decrease, but the distances are not limited thereto.

The respective detectors of the light receiver 112 may be arranged spirally with respect to the light emitter 111.

For example, the corresponding detectors among the light receiving groups, e.g., A1 of the first light receiving group, B1 of the second light receiving group, C1 of the third light receiving group, and D1 of the fourth light receiving group, may be spaced apart by predetermined angles from the light emitter 111. In the following description, detectors A1, B1, C1, and D1 may be referred to as a first corresponding group; detectors A2, B2, C2, and D2 may be referred to as a second corresponding group; detectors A3, B3, C3, and D3 may be referred to as a third corresponding group; and detectors A4, B4, C4, and D4 may be referred to as a fourth corresponding group.

Referring to FIG. 2, B1 is spaced apart from A1 by an angle of a1 from the light emitter 111; C1 is spaced apart from B1 by an angle of $\alpha_2$ from the light emitter 111; D1 is spaced apart from C1 by an angle of $\alpha_3$ from the light emitter 111. The angles $\alpha_1$, $\alpha_2$, and $\alpha_3$ may be measured from a reference line REF that connects the center of the light emitter 111 to a reference point on the fourth concentric circle D.

For convenience of explanation, FIG. 2 only illustrates angles among A1, B1, C1, and D1 of the first corresponding group, but the detectors of other corresponding groups may also be spaced apart by predetermined angles from the light emitter 111. For example, the angles, whereby the detectors A2 to D2 are spaced apart, may be equal to or different from the angles $\alpha_1$, $\alpha_2$, and $\alpha_3$.

The predetermined angles, whereby the corresponding detectors are spaced apart, may be equal to each other in a predetermined range, or may increase along a direction where radiuses of concentric circles increase, but are not limited thereto. In this case, the predetermined range may be greater than 0 degrees but smaller than 90 degrees, but is not limited thereto and may be changed variously according to the number of detectors included in the respective light receiving groups and the like.

For example, as illustrated in FIG. 2, when there are four light receiving groups and four corresponding groups, detectors of the respective corresponding groups may be spaced apart by equal angles within a range of 90 degrees. That is, the angles $\alpha_1$, $\alpha_2$, and $\alpha_3$ may be substantially the same or may be in a range of 22 degrees to 23 degrees, but are not limited thereto. In this case, a separation angle (e.g. angle between D1 and A2) may be equal to any one of separation angles (e.g., $\alpha_1$, $\alpha_2$, and $\alpha_3$) between the detectors in the respective corresponding groups, or may be smaller or greater than the angles.

In another example, the separation angles among the detectors in the corresponding groups may gradually increase along a direction where the radius of the concentric circles increases. That is, in FIG. 2, $\alpha_2$ may be greater than $\alpha_1$, and $\alpha_3$ may be greater than $\alpha_2$. In yet another example, the separation angles among the detectors in the corresponding groups may gradually decrease along a direction where the radius of the concentric circles increases. That is, in FIG. 2, $\alpha_2$ may be smaller than $\alpha_1$, and $\alpha_3$ may be smaller than $\alpha_2$. In this case the separation angle (e.g. angle between D1 and A2) between the corresponding groups may be equal to any one of separation angles among the detectors in the corresponding groups. However, the separation angle is not limited thereto, and may be greater or smaller than any one of the separation angles among the detectors.

As described above, as the respective detectors of the light receiver 112 are arranged spirally with respect to the light emitter 111, a space occupied by the optical sensor 110 may be used efficiently, and there is a less need for making the respective detectors smaller in size. If the size of the respective detectors is reduced excessively, their sensing performance may be degraded, such that by arranging the detectors as described above, the accuracy in estimating bio-information may be improved.

However, unlike the embodiment illustrated in FIG. 2, the corresponding detectors in the light receiving groups may be arranged in a straight line from the light emitter 111, as described above in FIG. 1. That is, the angle between the detectors in each corresponding group may be substantially zero.

Referring back to FIG. 1, the processor 120 may be connected to the optical sensor 110 electrically, mechanically, or by wired or wireless communication.

The processor 120 may control the light emitter 111. For example, in response to a user's manipulation, when a request for estimating bio-information is received and an object is placed on a cover surface of the optical sensor 110, the processor 120 may control an intensity and duration of light, and on/off of the light emitter 111.

For example, the processor 120 may control the light emitter 111 to emit light of different wavelengths simultaneously or in a time division manner according to elapsed time. In another example, the processor 120 may control the light emitter 111 to emit light continuously during a predetermined period of time (constant wave), or may control the light emitter 111 to emit light by pulse driving in order to reduce power consumption. However, the method of controlling the light emitter 111 by the processor 120 is not limited thereto and may be changed variously.

The processor 120 may control the respective light receiving groups of the light receiver 112. For example, the processor 120 may drive only some of the plurality of light receiving groups.

The processor 120 may selectively drive one of the light receiving groups based on a type of bio-information to be estimated. In this case, the type of bio-information to be estimated may be input by a user, or the bio-information to be estimated may be determined among the plurality of bio-information items, based on a contact force measured by a force sensor. The force sensor may be disposed on a lower end of the optical sensor 110. For example, the force sensor may be disposed on a side opposite to where the light is emitted from the light emitter 111, i.e., on a rear side of the substrate 113, so as to measure a force applied when a user presses the optical sensor 110.

For example, if the bio-information to be estimated first is heart rate, blood pressure, oxygen saturation, and stress, the processor 120 controls the light emitter 111 to emit light of at least one wavelength in corresponding wavelength ranges, e.g., green, red, and infrared wavelength ranges, and then may drive a light receiving group (e.g., light receiving group A or B in FIG. 2) which is disposed relatively close to the light emitter 111. Then, if the bio-information to be estimated next is an antioxidant index, the processor 120 may control the light emitter 111 to light emit in a corresponding range, e.g., a blue wavelength range, and then may drive a light receiving group (e.g., light receiving group C or D in FIG. 2) which is disposed relatively far away from the light emitter 111. However, the processor 120 is not limited thereto.

In another example, based further on at least one of a luminous intensity of a light source, a concentration range of bio-information to be estimated, an object's state or position, etc., the processor 120 may drive at least one light receiving group among the plurality of light receiving groups.

In this case, the processor 120 may use a luminous intensity (e.g., light emitting ability, power consumption) of a light source, a magnitude of reflected light, a concentration range of bio-information to be estimated, etc., as well as an equation such as the following Equation 1 which represents a relationship of separation distances between the light emitter 111 and the light receiving groups. In the following Equation 1, A denotes absorbance, Jo denotes a magnitude of incident light, I denotes a magnitude of the reflected light, c denotes an intrinsic absorption coefficient of a substance, c denotes the concentration of a substance to be estimated, and L denotes a distance between the light emitter 111 and the light receiving groups.

$$A = -\log\left(\frac{I}{I_0}\right) = -\log\left(\frac{\varepsilon c L}{I_0}\right)$$ [Equation 1]

For example, as the light emitter 111 is used for a predetermined period of time, a luminous intensity $I_0$ of the light source included in the light emitter 111 may be changed. For example, if a light emitting ability of the light source decreases, the processor 120 may drive a light receiving group, which is disposed closer to the light emitter 111, compared to a reference time point or an initial time point of use. However, the processor 120 is not limited thereto.

In another example, as a degree of light absorption varies according to the concentration of skin pigment of an object, the magnitude of the reflected light I may be changed significantly. As the skin color is darker, the magnitude of the reflected light I decreases, such that an optical signal measured by the light receiver 112 of the optical sensor 110 may be weak. By contrast, as the skin color is lighter, an optical signal measured by the light receiver 112 of the optical sensor 110 may be strong. An excessively small amount of optical signal is vulnerable to noise, such that desired bio-information may not be estimated accurately, and an excessively large amount of optical signal may cause overflow of a processing circuit while the optical signal is measured and processed by the light receiver 112. In this case, a bio-information estimation result may be inaccurate.

Accordingly, when the light emitter 111 emits light in skin tone measurement, the processor 120 may select at least one light receiving group for use in estimating bio-information based on a light measurement result of the respective light receiving groups of the light receiver 112.

In this case, if a measured light intensity of a specific detector is within a predefined threshold range, the processor 120 may select a light receiving group, which includes the detector, as a light receiving group for detecting an optical signal. Subsequently, the processor 120 may control the optical sensor 110 to drive the selected light receiving group.

For example, when there is a predetermined light receiving group for use in estimating bio-information, and if a measured light intensity of the predetermined light receiving group in skin tone measurement is less than a first threshold values, the processor 120 may select a light receiving group, which is closer to the light emitter 111 than the predetermined light receiving group, as a light receiving group for use in estimating bio-information.

Alternatively, if the measured light intensity of a predetermined light receiving group in skin tone measurement is greater than a second threshold, the processor 120 may select a light receiving group, which is further away from the light emitter 111 than the predetermined light receiving group, as a light receiving group for use in estimating bio-information.

Alternatively, if the measured light intensity of a predetermined light receiving group is greater than or equal to the first threshold value or less than or equal to the second threshold value, the processor 120 may select the predetermined light receiving group as a light receiving group for use in estimating bio-information. In this case, the first threshold value may be smaller than the second threshold value.

As described above, the processor 120 may detect an optical signal of an object in such a manner that if the object has a dark skin tone, the processor 120 may drive a light receiving group which is disposed closer to the light emitter 111, and if the object has a light skin tone, the processor 120 may drive a light receiving group which is disposed further away from the light emitter 111.

Among the plurality of light receiving groups, the processor 120 may drive two or more light receiving groups for estimating bio-information.

For example, by considering a type of bio-information to be estimated, a luminous intensity of a light source, a concentration range of bio-information to be estimated, an object's state or position, etc., if there is no light receiving group corresponding to the determined distance L between the light emitter 111 and the light receiving groups, the processor 120 may drive two light receiving groups corresponding to a concentric circle having a radius which is most similar to the distance L, and may use all of optical signals detected by the two driven light receiving groups.

In another example, if the object's skin absorbs a large amount of light such that a sufficient signal quality is not obtained, the processor 120 may drive two or more light receiving groups to achieve a sufficient signal quality. When the plurality of light receiving groups are driven, the optical sensor 110 may sequentially drive the respective light receiving groups in a time-division manner under the control of the processor 120, or may simultaneously drive the plurality of light receiving groups.

The respective detectors of at least one light receiving group, which is driven by the processor 120, may detect optical signals of the object based on light scattered or reflected from the object.

The processor 120 may receive data from the optical sensor 110 and may process the received data. In this case, upon receiving the optical signals from the driven light receiving group of the light receiver 112, the processor 120 may perform preprocessing, such as filtering for removing noise from the optical signal, amplifying the optical signal, converting the optical signal into a digital signal, and the like.

For example, the processor 120 may perform band-pass filtering between 0.4 Hz and 10 Hz by using a band-pass filter, to remove noise from the optical signal received from the optical sensor 110. Further, the processor 120 may correct the optical signal by reconstructing the optical signal based on Fast Fourier Transform.

In another example, the processor 120 may remove noise by applying a common mode filter. Further, the processor 120 may remove background noise by using a difference between a signal, measured when the light emitter 11 is turned on, and a signal measured when the light emitter 111 is turned off. However, the preprocessing is not limited thereto, and the processor 120 may perform various other preprocessing operations according to various measurement environments, such as computing performance or measurement accuracy of a device, purpose of bio-information estimation, a measured portion of a user, temperature and humidity of an object, temperature of the sensor part, and the like.

A separate analog circuit or digital circuit may also be used for the above preprocessing operations.

The processor 120 may estimate bio-information based on the optical signal detected by the driven light receiving group of the optical sensor 110. In this case, the bio-information may include at least one of heart rate, oxygen saturation, respiratory rate, triglyceride, blood pressure, arterial stiffness, skin age, blood vessel aging, blood glucose, electrolyte, carotenoid, body water, protein, alcohol, and antioxidant index. However, the bio-information is not limited thereto.

For example, the processor 120 may estimate bio-information by applying a pre-defined bio-information estimation model, as shown in the following Equation 2. The bio-information estimation model may be defined as various linear or non-linear combination functions, such as addition, subtraction, division, multiplication, logarithmic value, regression equation, and the like, with no specific limitation. For example, the following Equation 2 represents a simple linear function.

$$y = ax + b \quad \text{[Equation 2]}$$

In Equation 2, y denotes bio-information to be estimated, e.g., blood pressure, antioxidant index, and the like; x denotes a feature value in the optical signal detected by the driven light receiving group; and a and b may be coefficients for weighting the feature value, and may be fixed values universally applicable to a plurality of pre-defined users, or values adjusted for each user according to user characteristics. The value x may be any one or a combination of two or more of feature values. In this case, criteria for combining the feature values may be defined differently according to a type of body composition to be obtained, which may be defined properly for each user according to user characteristics.

For example, the processor 120 may obtain one or more feature values associated with blood pressure, such as a feature value associated with cardiac output, a feature value associated with total peripheral resistance, etc., from the optical signal detected by the driven light receiving group, e.g., the second light receiving group in FIG. 2, and may estimate a user's blood pressure by using the obtained feature values associated with blood pressure, or a value obtained by linearly or non-linearly combining the obtained values associated with blood pressure, and by using the above Equation 2. However, the estimation is not limited thereto.

In another example, the processor 120 may extract absorbance at a predetermined wavelength from the optical signal detected by the driven light receiving group, e.g., the third light receiving group in FIG. 2, and may determine an antioxidant index of the object by analyzing the extracted absorbance. The predetermined wavelength may be a blue wavelength in an absorption band of an antioxidant substance (e.g., carotenoid). In this case, the processor 120 may determine an antioxidant index of the object by using an antioxidant index estimation model. Here, the antioxidant index estimation model defines a relationship between the detected optical signal and the antioxidant index, and may be pre-obtained by regression analysis or machine learning and may be stored in an internal or external database of the processor 120. The antioxidant index estimation model may be generated in the form of a mathematical algorithm or a matching table, but is not limited thereto.

Figure 3:
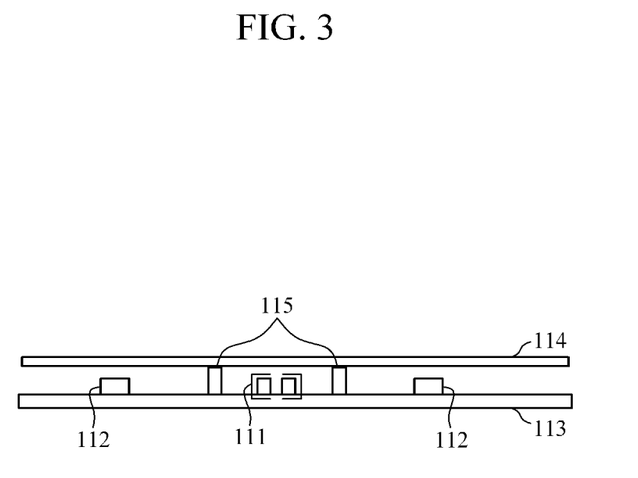
FIG. 3 is a cross-sectional view of an optical sensor according to an example embodiment of the present disclosure.

FIG. 3 is a cross-sectional view of an optical sensor according to an example embodiment of the present disclosure. In FIG. 3, the light emitter 111, the light receiver 112, the substrate 113, a cover surface 114, and a partition wall 115, which may be included in the optical sensor, are illustrated. The light emitter 111, the light receiver 112, and the substrate 113 are described in detail above with reference to FIGS. 1 and 2, such that the following description will be focused on the cover surface 114 and the partition wall 115.

The cover surface 114 may be a region coming into contact with an object. The cover surface 114 may include a light-transmitting region formed to allow light, emitted by the light emitter 111, to be directed toward the object. The light-transmitting region may be sealed by a cover made of a transparent material, such as glass, plastic, etc., so as to allow light to pass therethrough.

In this case, the cover surface 114 may be formed independently on each of the light emitter and the light receiver, so as to prevent light, emitted by the light emitter 111, from being directly leaking into the light receiver 112.

A size of the cover surface 114 may be determined based on a size of the plurality of light receiving groups of the light receiver 112. For example, the cover surface 141 may have a size which is greater than or equal to a diameter of a largest concentric circle, for example, 2d of FIG. 2, among the plurality of concentric circles on which the plurality of light receiving groups are arranged. However, the size of the cover surface 114 is not limited thereto.

The cover surface 114 may have a polygonal shape, such as a circle, triangle, square, and the like. In this case, if the plurality of light receiving groups are arranged on the respective concentric circles, the cover surface 114 may be formed in a circular shape, but the shape is not limited thereto.

The cover surface 114 may include a Fresnel lens, a retroreflector, a cover glass coated with an anti-reflective coating, etc., so as to prevent the light emitter 111 and the light receiver 112 from being seen with the naked eye from the outside and to improve light efficiency.

The partition wall 115 may be disposed between the light emitter 111 and the light receiver 112 on the substrate 113. For example, the partition wall 115 may be disposed between the light emitter 111 and a smallest concentric circle, on which the first light receiving group is disposed, among the plurality of concentric circles of FIG. 2, but the position of the partition wall 115 is not limited thereto. The partition wall 115 may block light, emitted by the light emitter 111, from being directly directed toward the respective detectors of the light receiver 112.

The optical sensor may further include at least one optical element, e.g., lens and the like, for allowing light, reflected or scattered from the object, to be directed toward the light receiver 120.

Figure 4:
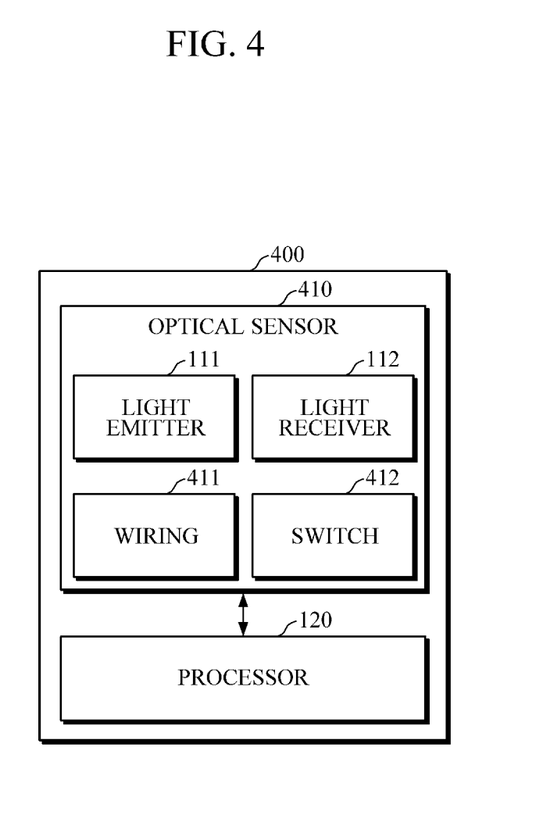
FIG. 4 is a block diagram illustrating an apparatus for estimating bio-information according to another example embodiment of the present disclosure.

FIG. 4 is a block diagram illustrating an apparatus for estimating bio-information according to another example embodiment of the present disclosure. Referring to FIG. 4, the apparatus 400 for estimating bio-information may include an optical sensor 410 and the processor 120. The optical sensor 410 may further include wiring 411 and a switch 412, in addition to the light emitter 111 and the light receiver 112 described above in FIG. 1.

The wiring 411 may mutually connect the plurality of detectors in the respective light receiving groups. For example, the wiring 411 may mutually connect A1, A2, A3, and A4 of the first light receiving group in FIG. 2. The wiring 411 may include a plurality of wires, and a set of light detectors disposed on the same circle (e.g., light detectors A1-A4 disposed on the circle A) may be connected to the same wire, so that the processor 120 may turn on or turn off the set of light detectors connected to the same wire all together.

In this case, the processor 120 may simultaneously receive optical signals detected by the respective detectors A1, A2, A3, and A4 which are connected by the wiring in the driven light receiving group, e.g., the first light receiving group in FIG. 2. The processor 120 may perform preprocessing, including averaging, normalization, etc., on the received respective optical signals, and may derive a new optical signal by combining the respective optical signals.

The switch 412 may individually control the respective detectors of the respective light receiving groups. In this case, the switch 412 may individually control the respective detectors, a transimpedance amplifier (TIA) for filtering and amplifying signals photoelectric converted by the detectors, and a converter for converting an analog signal into a digital signal.

For example, when driving the first light receiving group in FIG. 2, the processor 120 may control the switch 412 of the first light receiving group to individually connect the detectors A1, A2, A3, and A4 of the first light receiving group with the transimpedance amplifier and the converter. In this case, the processor 120 may sequentially connect the detectors A1, A2, A3, and A4 of the first light receiving group with the transimpedance amplifier and the converter according to elapsed time, or may connect only some of the detectors A1, A2, A3, and A4 of the first light receiving group with the transimpedance amplifier and the converter.

Figure 5:
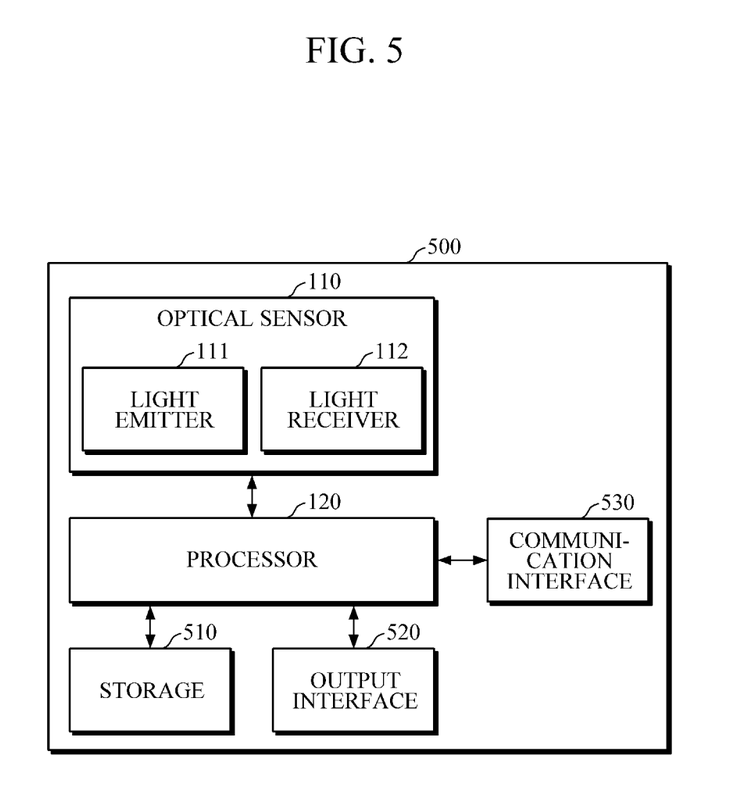
FIG. 5 is a block diagram illustrating an apparatus for estimating bio-information according to another example embodiment of the present disclosure.

FIG. 5 is a block diagram illustrating an apparatus for estimating bio-information according to another example embodiment of the present disclosure. Referring to FIG. 5, an apparatus 500 for estimating bio-information may further include a storage 510, an output interface 520, and a communication interface 530 in the apparatus 100 for estimating bio-information of FIG. 1.

The storage 510 may store reference information required for estimating bio-information, and processing results of the optical sensor 110 and/or the processor 120. In this case, the reference information may include separation distances, which are predetermined for each bio-information, between the light emitter 111 and the light receiving groups, luminous intensity information of a light source, a concentration range of each bio-information to be estimated, an object's state or position, user information such as a user's age, gender, health condition, and the like, a normal contact state such as a contact position of an object, light source driving conditions, a bio-information estimation model, etc., but is not limited thereto.

In this case, the storage 510 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Upon obtaining an estimated bio-information value, the output interface 520 may visually display the estimated bio-information value on a display. In this case, if the estimated bio-information value falls outside a normal range, the output interface 520 may visually display alarm/warning information. Alternatively, the output interface 520 may output warning information regarding a contact state, a contact force, and the estimated bio-information value, by using a non-visual output means such as an audio device or a haptic device.

The communication interface 530 may communicate with an external device under the control of the processor 120 to transmit and receive various data related to estimating bio-information.

For example, the communication interface 530 may transmit processing results of the processor 120 and the like to the external device, so as to allow the external device to manage a bio-information history, to monitor a user's health condition, to output the bio-information history and a health condition monitoring result, and the like. In this case, the external device may include a smartphone, a tablet PC, a desktop computer, a laptop computer, a TV, a home monitor, a refrigerator panel monitor, etc., or devices used in medical institutions such as a cuff-type blood pressure measuring device, a body composition measuring device, and the like, but is not limited thereto.

In another example, the communication interface 530 may receive, from the external device, separation distances, which are predetermined for each bio-information, between the light emitter and the light receiving groups, a reference luminous intensity of a light source, an upper limit and a lower limit of a concentration range of a bio-information to be estimated, a bio-information estimation model required for estimating bio-information, user characteristic information, and the like. The received information may be stored in the storage 510.

In this case, the communication interface 530 may communication with external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G, 4G, and 5G communications, and the like. However, this is merely exemplary and is not intended to be limiting.

Figure 6:
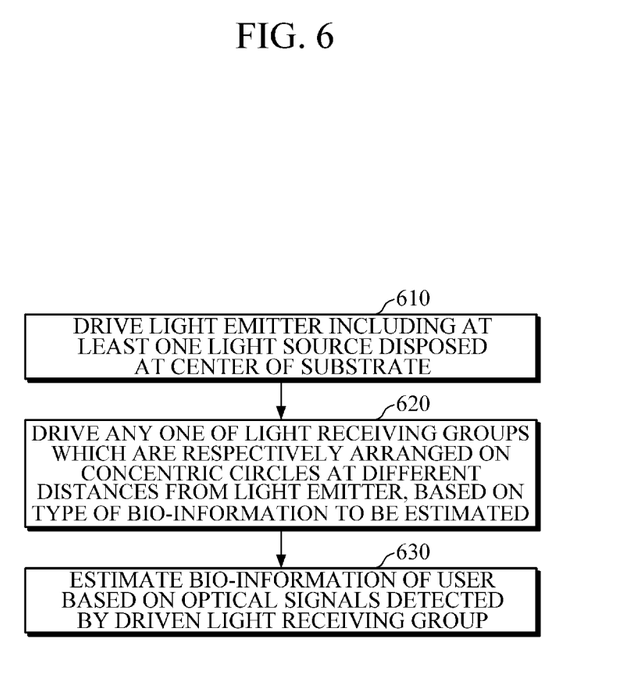
FIG. 6 is a flowchart illustrating a method of estimating bio-information according to an example embodiment of the present disclosure.

FIG. 6 is a flowchart illustrating a method of estimating bio-information according to an example embodiment of the present disclosure. The method of FIG. 6 is an example of a method of estimating bio-information which is performed by the apparatuses 100, 400, and 500 for estimating bio-information of FIGS. 1, 4, and 5, which are described in detail above, and thus will be briefly described below to avoid redundancy.

First, the apparatus for estimating bio-information may drive the light emitter including at least one light source disposed at the center of the substrate in operation 610. For example, the apparatus for estimating bio-information may control the light emitter to emit light of different wavelengths over time. In another example, the apparatus for estimating bio-information may control the light emitter to emit light continuously during a predetermined period of time (constant wave), or may control the light emitter to emit light by pulse driving in order to reduce power consumption.

Then, based on a type of bio-information to be estimated, the apparatus for estimating bio-information may drive any one of the light receiving groups which are respectively arranged on a plurality of concentric circles at different distances from the light emitter in operation 620. In this case, the respective detectors of each light receiving group may be outraged spirally with respect to the light emitter. For example, the corresponding detectors among the light receiving groups may be spaced apart by predetermined angles from the light emitter. A detailed description thereof will be omitted.

For example, among the plurality of light receiving groups, the apparatus for estimating bio-information may drive a light receiving group corresponding to separation distances, which are predetermined for each bio-information, between the light emitter and the light receiving groups.

In another example, based further on at least one of a luminous intensity of a light source, a concentration range of bio-information to be estimated, an object's state or position, etc., the apparatus for estimating bio-information may drive any one light receiving group among the plurality of light receiving groups.

In an example embodiment, the apparatus for estimating bio-information may display a plurality of bio-information measurement modes, including an antioxidant index measurement mode, a heart rate measurement mode, and a PPG measurement mode. When a user selects the antioxidant index measurement mode, the apparatus may activate the light detectors D1 D4 of the fourth light receiving group and may turn off the rest of the light detectors A1-A4, B1-B4, and C1-C4 while the light emitter 111 is emitting light so as to collect the light from the light detectors D1-D4. When the user selects the heart rate measurement mode, the apparatus may activate the light detectors C1-C4 of the third light receiving group and may turn off the rest of the light detectors A1-A4, B1-B4, and D1-D4 while the light emitter 111 is emitting light so as to collect the light from the light detectors C1-C4. When the user selects the PPG measurement mode, the apparatus may activate the light detectors B1-B4 of the second light receiving group and may turn off the rest of the light detectors A1-A4, C1-C4, and D1-D4 while the light emitter 111 is emitting light so as to collect the light from the light detectors B1-B4. Alternatively, the same light detectors B1-B4 or C1-C4 may be used for both the heart rate measurement mode and the PPG measurement mode.

According to experiments conducted to measure performance (e.g., a coefficient of determination $R^2$) of a plurality of different types of optical biosensors, such as an antioxidant sensor, a PPG sensor, and a heart rate monitoring sensor, the optimal distance from a light emitter to a light detector (i.e., an emitter-to-detector distance) for acquiring the best performance (i.e., the highest estimation accuracy) varies according to the types of the optical biosensors. For example, the emitter-to-detector distance for acquiring the best performance of the antioxidant sensor is greater than the emitter-to-detector distance for acquiring the best performance of the PPG sensor and the heart rate monitoring sensor. Accordingly, the apparatus according to an example embodiment of the present disclosure selectively activates the light detectors which have the emitter-to-detector distance corresponding to the type of bio-information to be measured, so as to obtain the best performance.

Subsequently, the apparatus for estimating bio-information may estimate bio-information of a user based on the optical signals detected by the driven light receiving group in operation 630.

Figure 7:
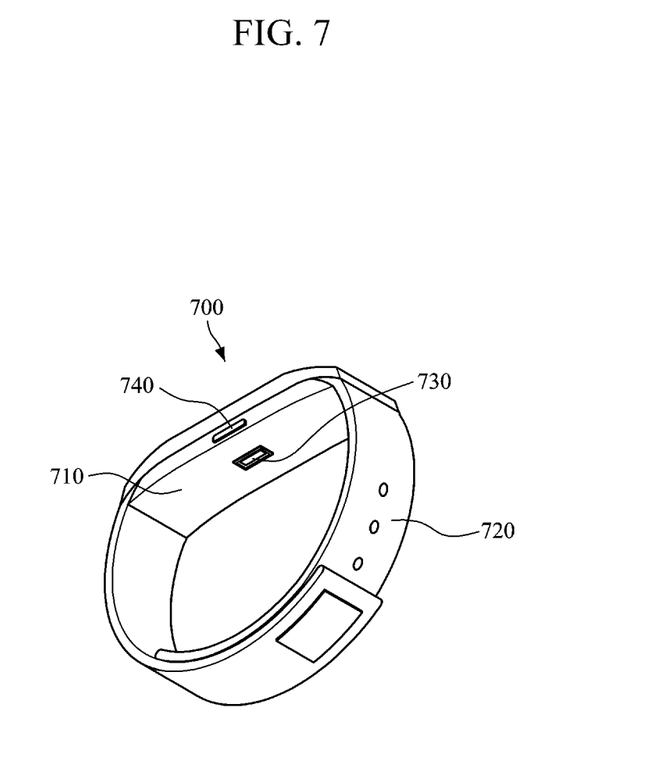
FIG. 7 is a diagram illustrating a wearable device according to an example embodiment of the present disclosure.

FIG. 7 is a diagram illustrating a wearable device according to an example embodiment of the present disclosure. The wearable device 700 may include various embodiments of the aforementioned apparatuses 100, 400, and 500 for estimating bio-information.

Referring to FIG. 7, the wearable device 700 includes a main body 710 and a strap 720.

The strap 720 may be connected to both ends of the main body 710, and may be flexible so as to be wrapped around a user's wrist. The strap 720 may be composed of a first strap and a second strap which are separated from each other. One ends of the first strap and the second strap are connected to the main body 710, and the other ends thereof may be connected to each other via a fastening means. In this case, the fastening means may be formed as magnetic fastening, Velcro fastening, pin fastening, and the like, but is not limited thereto. Further, the strap 720 is not limited thereto, and may be integrally formed as a non-detachable band.

In this case, air may be injected into the strap 720 or the strap 720 may be provided with an air bladder, so as to have elasticity according to a change in pressure applied to the wrist, and the change in pressure of the wrist may be transmitted to the main body 710.

A battery may be embedded in the main body 710 or the strap 720 to supply power to the wearable device 700.

In addition, a sensor part 730 may be mounted on one side of the main body 710. The sensor part 730 may include an optical sensor, a force sensor, a PPG sensor, an impedance sensor, a motion sensor, a gyro sensor, and the like. In this case, the optical sensor may include a light emitter disposed at the center of the substrate, and a light receiver including a plurality of light receiving groups which are respectively arranged on a plurality of concentric circles at different distances from the light emitter. A detailed description thereof will be omitted.

The processor may be mounted in the main body 710. The processor may drive the light emitter of the optical sensor, and then may drive any one of the light receiving groups based on a type of bio-information to be estimated, and may estimate bio-information of a user based on the optical signals detected by the driven light receiving group. A detailed description thereof will be omitted.

An output interface may be mounted on a front surface of the main body 710. The output interface may provide, for example, a bio-information estimation result for a user through a display and the like.

A storage may be included in the main body 710, and may store information processed by the processor and reference information for estimating bio-information.

In addition, the wearable device 700 may include a manipulator 740 for receiving a user's control command and transmitting the received control command to the processor.

The manipulator 740 may have a function of inputting a command to turn on/off the wearable device 700.

Moreover, the wearable device 700 may include a communication interface for transmitting and receiving various data with an external device, and various other modules for performing additional functions provided by the wearable device 700.

Figure 8:
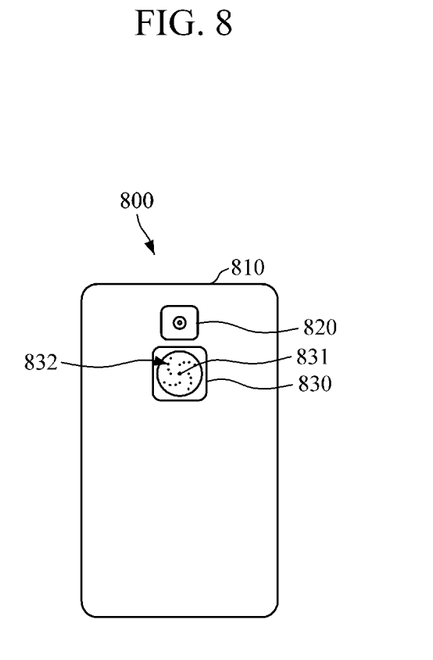
FIG. 8 is a diagram illustrating a smart device according to an example embodiment of the present disclosure.

FIG. 8 is a diagram illustrating a smart device according to an example embodiment of the present disclosure. In this case, the smart device 800 may include various embodiments of the aforementioned apparatuses 100, 400, and 500 for estimating bio-information. In this case, the smart device may include a smartphone, a tablet PC, and the like.

Referring to FIG. 8, the smart device 800 includes a main body 810 and a sensor part 830 mounted on one surface of the main body 810. The sensor part 830 may include an optical sensor and a force sensor, in which the optical sensor may include a light emitter 831 having one or more light sources, and a light receiver 832 having a plurality of light receiving groups which are respectively arranged on a plurality of concentric circles at different distance from the light emitter. In this case, the respective detectors of the plurality of light receiving groups of the light receiver 832 may include a CIS image sensor. As illustrated in FIG. 8, the sensor part 830 may be mounted on a rear surface of the main body 810, but is not limited thereto. Further, the sensor part 830 may include an auxiliary sensor, such as an impedance sensor, a motion sensor, a gyro sensor, and the like.

The processor may be mounted in the main body 810. The processor may drive any one of the light receiving groups, based on a type of bio-information to be estimated, and may estimate bio-information of a user based on the optical signals detected by the driven light receiving group. A detailed description thereof will be omitted.

In addition, the main body 810 may include an image sensor 820 as illustrated in FIG. 8. When a user's object, e.g., a finger, approaches the sensor part 830 to measure an optical signal, the image sensor 820 may capture an image of the finger and may transmit the captured image to the processor. In this case, based on the image of the finger, the processor may identify a relative position of the finger with respect to an actual position of the sensor part 830, and may provide a graphic object including guide information on the relative position of the finger to the user through the output interface.

In addition, a storage, a communication interface, and the like may be included in the main body 810, to store bio-information estimated by the processor or to transmit the estimated bio-information to other external devices. Various other modules for performing various functions may be mounted in the main body 810.

The present invention can be realized as a computer-readable code written on a computer-readable recording medium. The computer-readable recording medium may be any type of recording device in which data is stored in a computer-readable manner.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating bio-information, the apparatus comprising:
    an optical sensor comprising a light emitter disposed on a substrate, and a plurality of light receiving groups which are arranged on a plurality of concentric circles on the substrate, at different distances from the light emitter in a radial direction, respectively; and
    a processor configured to drive one of the plurality of light receiving groups that is selected based on a type of the bio-information to be estimated, and estimate the bio-information of an object based on optical signals detected by the driven light receiving group,
    wherein a plurality of detectors included in each of the plurality of light receiving groups are spaced apart from each other by a predetermined angle on a corresponding one of the plurality of concentric circles, and
    wherein each of the plurality of detectors in one of the plurality of light receiving groups does not align with any other detectors in the other plurality of light receiving groups, in the radial direction.

2. The apparatus of claim 1, wherein the predetermined angle by which the plurality of detectors are spaced apart from each other, is set differently for each of the plurality of light receiving groups that are provided on the plurality of concentric circles.

3. The apparatus of claim 1, wherein a reference line extends from a center of the plurality of concentric circles to a point on a largest concentric circle among the plurality of concentric circles, and
    wherein the plurality of detectors of the plurality of light receiving groups are located at different angles from the reference line.

4. The apparatus of claim 1, wherein each of the plurality of light receiving groups comprises a same number of detectors.

5. The apparatus of claim 1, wherein the plurality of detectors in each of the plurality of light receiving groups are arranged symmetrical to each other with respect to the light emitter.

6. The apparatus of claim 1, wherein among the plurality of concentric circles, a radius of a smallest concentric circle is greater than or equal to 2 mm, and a radius of a largest concentric circle is smaller than or equal to 6 mm.

7. The apparatus of claim 1, wherein among the plurality of light receiving groups, the processor drives a light receiving group corresponding to separation distances, which are predetermined for each bio-information, between the light emitter and the plurality of light receiving groups.

8. The apparatus of claim 1, wherein the plurality of light receiving groups comprises a first light receiving group and a second light receiving group, and the first light receiving group is disposed closer to the light emitter than the second light receiving group is, and
   wherein the processor is further configured to:
      based on a request to estimate the bio-information including at least one of heart rate, blood pressure, oxygen saturation, and stress, drive the first light receiving group to estimate the bio-information, and
      based on a request to estimate the bio-information including an antioxidant index, driver the second light receiving group to estimate the bio-information.

9. The apparatus of claim 1, wherein the optical sensor further comprises wiring that connects the plurality of detectors in each of the plurality of light receiving groups,
   wherein the processor receives the optical signals detected by the plurality of detectors which are connected by the wiring in the driven light receiving group.

10. The apparatus of claim 1, wherein the optical sensor further comprises a switch configured to individually control connection to the plurality of detectors included in each of the plurality of light receiving groups, a transimpedance amplifier configured to filter and amplify analog signals photoelectric converted by the plurality of detectors, and a converter configured to convert the analog signals into digital signals.

11. The apparatus of claim 1, wherein the optical sensor further comprises a partition wall disposed between the light emitter and the plurality of light receiving groups on the substrate.

12. The apparatus of claim 1, further comprising a cover surface configured to be contacted by contact with the object,
   wherein the cover surface has a size greater than or equal to a diameter of a largest concentric circle, among the plurality of concentric circles.

13. The apparatus of claim 1, further comprising a cover surface coming into contact with the object,
   wherein the cover surface has at least one of Fresnel lens, a retroreflector, and a cover glass coated with an anti-reflective coating.

14. The apparatus of claim 1, wherein the processor is configured to:
   drive a first light receiving group, among the plurality of light receiving groups;
   based on a determination that light intensities of the optical signals detected by the first light receiving group are less than a threshold value, drive a second light receiving group which is closer to the light emitter than the first light receiving group is, among the plurality of light receiving groups; and
   estimate the bio-information of the object based on the optical signals detected by the second light receiving group.

15. A method of estimating bio-information, the method comprising:
   driving a light emitter including at least one or more light sources disposed at a center of a substrate;
   based on a type of bio-information to be estimated, driving one of a plurality of light receiving groups which are respectively arranged on a plurality of concentric circles at different distances from the light emitter in a radial direction; and
   estimating the bio-information of a user based on optical signals detected by the driven light receiving group,
   wherein a plurality of detectors included in each of the plurality of light receiving groups are spaced apart from each other by a predetermined angle on a corresponding one of the plurality of concentric circles, and
   wherein each of the plurality of detectors in one of the plurality of light receiving groups does not align with any other detectors in the other plurality of light receiving groups, in the radial direction.

16. An optical sensor comprising:
   a light emitter including at least one or more light sources disposed at a center of a substrate; and
   a plurality of light receiving groups which are respectively arranged on a plurality of concentric circles on the substrate, at different distances from the light emitter in a radial direction,
   wherein a plurality of detectors included in each of the plurality of light receiving groups are spaced apart from each other by a predetermined angle on a corresponding one of the plurality of concentric circles, and
   wherein each of the plurality of detectors in one of the plurality of light receiving groups does not align with any other detectors in the other plurality of light receiving groups, in the radial direction.

17. The optical sensor of claim 16, wherein the predetermined angle by which the plurality of detectors are spaced apart from each other, is set differently for each of the plurality of light receiving groups that are provided on the plurality of concentric circles.

18. The optical sensor of claim 16, wherein a reference line extends from the center of the substrate to a point on a largest concentric circle among the plurality of concentric circles, and
   wherein the plurality of detectors of the plurality of light receiving groups are located at different angles from the reference line.

19. The optical sensor of claim 16, wherein each of the plurality of light receiving groups comprises a same number of detectors.

20. The optical sensor of claim 16, wherein the plurality of detectors in each of the plurality of light receiving groups are arranged symmetrical to each other with respect to the light emitter.

* * * * *